US006854847B2

(12) United States Patent
Lai et al.

(10) Patent No.: US 6,854,847 B2
(45) Date of Patent: Feb. 15, 2005

(54) OPTICAL TRACKING DEVICE EMPLOYING SCANNING BEAMS ON SYMMETRIC REFERENCE

(76) Inventors: Ming Lai, P.O. Box 10845, Pleasanton, CA (US) 94588; Mei Juan Yuan, 5615 Cedar Crest Ter., Dublin, CA (US) 94568

( * ) Notice: Subject to any disclaimer, the term of this patent is extended or adjusted under 35 U.S.C. 154(b) by 224 days.

(21) Appl. No.: 10/294,392

(22) Filed: Nov. 13, 2002

(65) Prior Publication Data

US 2003/0090626 A1 May 15, 2003

Related U.S. Application Data

(60) Provisional application No. 60/338,029, filed on Nov. 13, 2001, and provisional application No. 60/360,979, filed on Mar. 1, 2002.

(51) Int. Cl.[7] ................................................. A61B 3/14
(52) U.S. Cl. ........................................................ 351/210
(58) Field of Search ............................... 351/205, 206, 351/208, 209, 210, 216, 217, 221, 246; 606/4, 5, 10; 250/235; 356/445–447; 359/385

(56) References Cited

U.S. PATENT DOCUMENTS

| | | | | | |
|---|---|---|---|---|---|
| 4,764,005 | A | * | 8/1988 | Webb et al. ................. 351/205 |
| 5,098,426 | A | * | 3/1992 | Sklar et al. ..................... 606/5 |
| 5,345,281 | A | * | 9/1994 | Taboada et al. ............. 351/210 |
| 5,360,424 | A | * | 11/1994 | Klopotek ........................ 606/5 |
| 5,410,376 | A | * | 4/1995 | Cornsweet et al. .......... 351/210 |
| 5,430,505 | A | * | 7/1995 | Katz ........................... 351/208 |
| 5,620,436 | A | * | 4/1997 | Lang et al. ..................... 606/4 |
| 5,632,742 | A | * | 5/1997 | Frey et al. ...................... 606/4 |
| 5,645,550 | A | * | 7/1997 | Hohla ............................ 606/1 |
| 5,752,950 | A | * | 5/1998 | Frey et al. ...................... 606/4 |
| 5,782,822 | A | * | 7/1998 | Telfair et al. ................... 606/5 |
| 5,865,832 | A | * | 2/1999 | Knopp et al. ................. 606/10 |
| 5,966,197 | A | * | 10/1999 | Yee .............................. 351/210 |
| 5,980,513 | A | * | 11/1999 | Frey et al. .................... 606/10 |
| 6,179,422 | B1 | * | 1/2001 | Lai .............................. 351/210 |
| 6,299,307 | B1 | * | 10/2001 | Oltean et al. ................ 351/210 |
| 6,302,879 | B1 | * | 10/2001 | Frey et al. ...................... 606/5 |
| 6,315,773 | B1 | * | 11/2001 | Frey et al. ...................... 606/4 |
| 6,604,825 | B2 | * | 8/2003 | Lai et al. ..................... 351/210 |
| 2001/0035938 | A1 | * | 11/2001 | Lai et al. ..................... 351/209 |
| 2002/0013573 | A1 | * | 1/2002 | Telfair et al. ................... 606/5 |
| 2003/0090626 | A1 | * | 5/2003 | Lai et al. ..................... 351/209 |

* cited by examiner

*Primary Examiner*—Brian L. Casler
*Assistant Examiner*—John R. Sanders

(57) ABSTRACT

The optical tracking device of the present invention is contemplated to obtain a large tracking range in an open loop configuration. The tracking device projects and scans two probe beams across a symmetric reference landmark that has at least two symmetric lines or axes. The two probe beams scan repeatedly and alternatively along two directions of which each is perpendicular to a symmetric line of the reference mark. For each scan, a substantially symmetric profile is generated in the scattered light as the beam scans across the boundary on each side of the symmetric reference. This symmetric profile in the scattered light is detected and used to determine the position of the related symmetric line. The position detection of the symmetric line is independent from the object's movement along the direction of the symmetric line. The scattered-light signal from the two probe beams is separated by synchronized detection in the time domain. This way, the two probe beams scan and sense the positions of two symmetric lines and then the crossing point between the two lines determines the lateral position of the object to be tracked. The two symmetric lines may or may not be perpendicular to each other. The range of this detection is substantially as large as the size of the reference landmark.

19 Claims, 6 Drawing Sheets

FIGURE 3
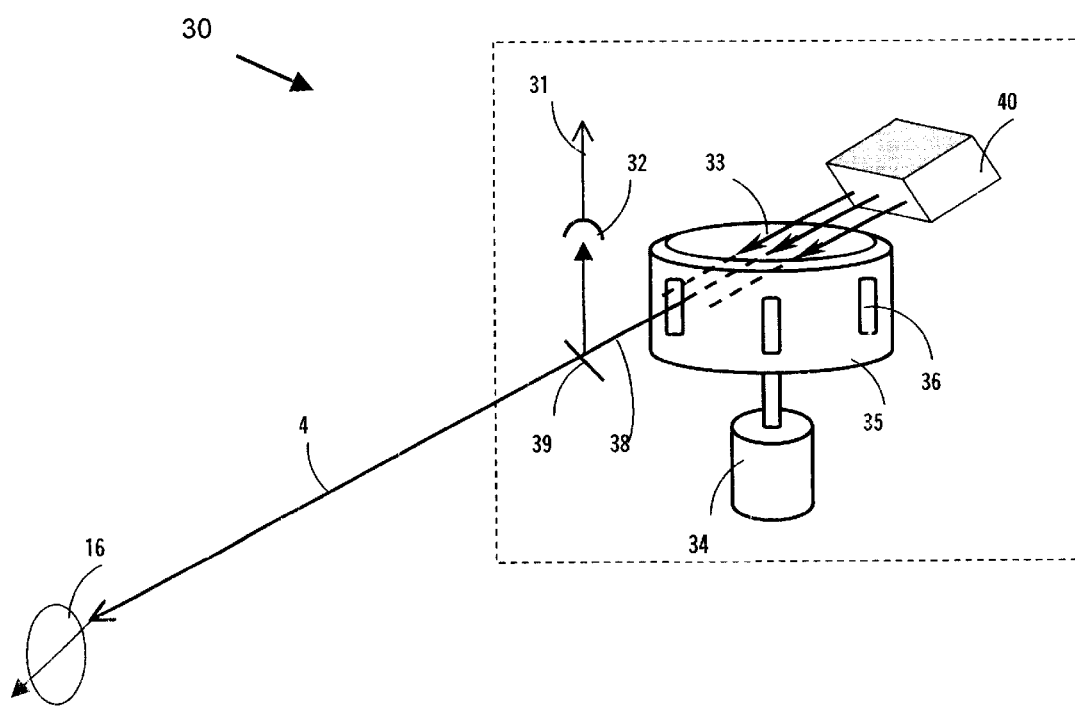
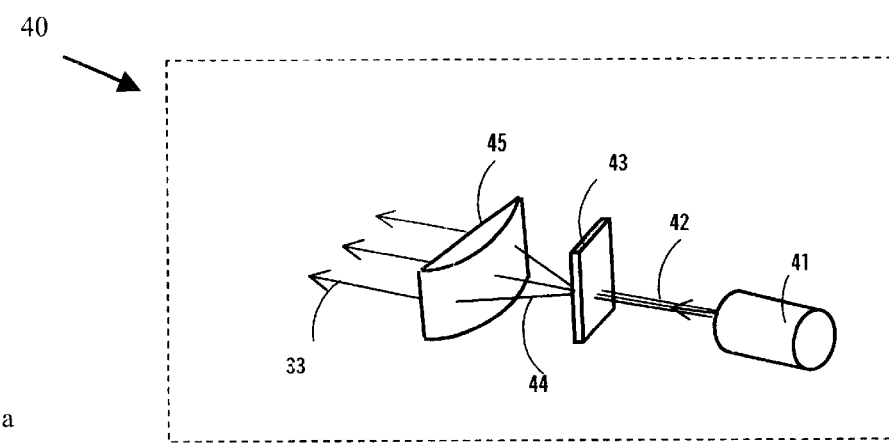
FIGURE 3a

OPTICAL TRACKING DEVICE EMPLOYING SCANNING BEAMS ON SYMMETRIC REFERENCE

This application claims the benefit of U.S. provisional application No. 60/338,029, filed on Nov. 13, 2001, and U.S. provisional application No. 60/360,979, filed on Mar. 1, 2002.

TECHNICAL FIELD

The present invention relates to an optical tracking device that tracks the lateral displacement of an object that has a symmetric reference landmark with at least two symmetric axes. In particularly, the present invention relates to an optical tracking device that tracks the lateral displacement of a subject's eye during a laser refractive surgery.

BACKGROUND

In U.S. Pat. No. 6,179,422 to Lai, an optical tracking device is described to employ two scanning beams to scan across boundaries of a reference mark affixed on an object to be tracked. In an embodiment of eye tracking, the device projects two beams scanning across the limbus at 12 and 3 o'clock positions, respectively. The device detects the timing of the probe beam scanning across the limbus and thus determines the lateral position of the subject's eye.

Two configurations have been described in U.S. Pat. No. 6,179,422 to implement the tracking device. The first one is of open loop, in which the scanning probe beam does not follow the movement of the eye. The second one is of closed loop, in which both the surgical laser beam and the probe beam follow the movement of the tracked eye.

The advantage of the open loop configuration is its simplicity and its feasibility to separate the optical path for position sensing from the optical path for the surgical laser beam. The tracking device can thus be a stand-alone module. Its disadvantage is a limited tracking range due to the curved nature of the limbus, which is the tracking mark for the tracking device of U.S. Pat. No. 6,179,422. The movement detection along two orthogonal directions is no longer independent in an open loop configuration when each probe beam does not intersect perpendicularly with respect to the curved mark such as the limbus.

The advantage of the closed loop configuration is to have much larger tracking range while having both the probe beam and the surgical beam deflected via a common beam steering module. The movement detection along the two orthogonal directions is basically independent in a closed loop configuration because the probe beams have no significant displacement with respect to the limbus. On the other hand, using a common beam steering module for both the surgical and the probe beams introduces a couple of limitations. First, the surgical laser beam has a more complex optical assembly, including the common beam steering module. Second, a bigger mirror is required for the common beam steering module to accommodate both the surgical and the probe beams, while a bigger mirror means a slower system response.

SUMMARY

In this application, a new and improved optical tracking device is contemplated to obtain a large tracking range in an open loop configuration. The new optical tracking device projects and scans two probe beams across a symmetric reference landmark that has at least two symmetric lines or axes and that has well distinguishable reflectance from the surrounding area. The two probe beams scan repeatedly and alternatively along two directions of which each is perpendicular to a symmetric line of the reference mark. For each scan, a substantially symmetric profile is generated in the scattered light as the beam scans across the boundary on each side of the symmetric reference. This symmetric profile in the scattered light is detected and used to determine the position of the related symmetric line. The position detection of the symmetric line is independent from the object's movement along the direction of the symmetric line. The scattered-light signal from the two probe beams is separated by synchronized detection in the time domain. This way, the two probe beams scan and sense the positions of two symmetric lines and then the crossing point between the two lines determines the lateral position of the object to be tracked. The two symmetric lines may or may not be perpendicular to each other. The range of this detection is substantially as large as the size of the reference landmark.

The optical tracking device of the present invention can be used for tracking eye movement for applications in eye surgery and diagnosis, using the pupil or limbus as the symmetric reference mark. In a preferred embodiment of pupil tracking, the optical tracking device tracks the eye pupil, which has generally two symmetric lines along, for instance, x and y directions respectively. In this preferred embodiment, one scanning beam scans along y direction to determine the position of the symmetric line x, i.e. the x-axis, while the other scanning beam scans along x direction to determine the position of the symmetric line y, i.e. the y-axis. Each beam scans repeatedly along its own direction and the two beam shall scan alternatively from each other.

The scanning beams are projected from a direction close to the eye axis, and the scattered light from the eye is collected and detected at a direction also close to the scanning beam. Due to the cat eye or red eye effect, the detected signal increases sharply as the beam scans across the boundary from the iris to the pupil and decreases sharply as the beam scans from the pupil to the iris. For each scan, therefore, the detected signal is substantially a square pulse and the leading edge and tracing edge correspond to the positions of the reference boundary between the iris and the pupil. For a scan along the x direction, the center of the square pulse corresponds to the position of the y-axis and the detection is independent to the eye position along y direction. Similarly, a scan along y direction can detect the x-axis independent to the eye position along x direction.

In the preferred embodiment, the two scanning beams scan alternatively and thus separate from each other in time. Therefore, detection signals of the scattered light from the two beams can be separated in the time domain. Scattered light from both scanning beams is collected and focused into one fast photo-detector. The two scanning beams scan across the pupil alternatively to generate two trains of square-like pulses without any pulse overlapping. The device also produces one train of trig pulses to synchronize with each of the scanning beams and to set a timing reference for each scanning beam position. In any given moment, the timing center of a square-like pulse stemmed from a scan along x direction determines the x position of the pupil, while the timing center of a square-like pulse stemmed from a scan along y direction determines the y position of the pupil.

With the positioning signals detected above, a computer can then generate a control signal to steer a surgical laser beam to follow the movement of the eye. The tracking range of the device is substantially the size of the symmetric reference mark, i.e. the subject pupil.

Accordingly, an advantage of this optical tracking device is an enlarged tracking range in an open-loop configuration.

Another advantage of this optical tracking device is its independent position detection of two symmetric lines of a reference landmark A further advantage of this optical tracking device is its simple implementation of pupil tracking for applications in eye diagnosis and surgery.

The above and other objectives and advantages of the invention will become more apparent in the following drawings, detailed description, and claims.

BRIEF DESCRIPTION OF THE DRAWINGS

FIG. 3 is a schematic diagram showing a probe beam projector.

FIG. 3a shows schematically a line beam generator.

DETAILED DESCRIPTION

Figures 1, 1A:
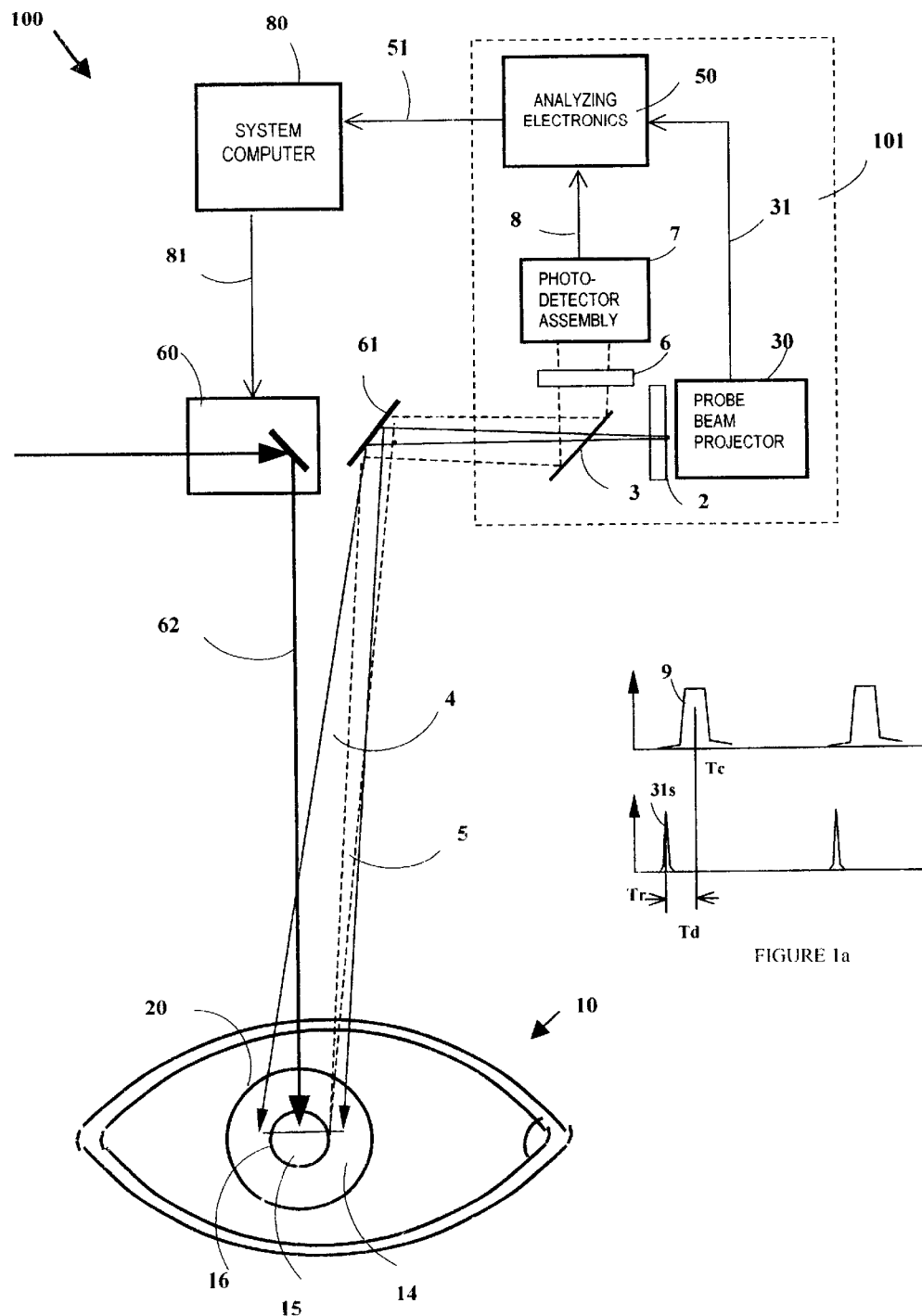
FIG. 1 is a schematic diagram of an optical tracking device in an open loop configuration for a surgical laser beam delivery system, in accordance with one embodiment of the present invention.
FIG. 1a shows timing diagrams of the scattered-light signal from the eye and the reference signal generated by a probe beam projector.

FIG. 1 is a schematic diagram of an optical tracking device 101 in an open loop configuration for a surgical laser beam delivery system 100, in accordance with on embodiment of the present invention. The beam delivery system 100 implements an open loop configuration that includes a tracking device 101, a system computer 80, a surgical laser beam 62, and a beam steering module 60 (e.g., a x-y scanner). The tracking device 101 projects a scanning probe beam 4 and monitors the position of the eye 10. Using the eye positioning data from the tracking device 101, the system computer 80 controls the beam steering module 60 to direct the surgical laser beam 62 to follow the eye movement and to impinge on predetermined position on the eye 10. As an open loop configuration, the scanning probe beam 4 does not follow the movement of the eye 10 and only one beam steering module 60 is required.

For illustration purpose, the tracking device 101 shown in FIG. 1 projects only a first probe beam 4 scanning along one direction and thus monitors only one-dimension of eye movement (e.g., along x-direction). To determine the eye's movement in two dimensions, a second scanning probe beam is needed to monitor the movement of the eye 10 along a second different direction, e.g., the y-direction orthogonal to the x-direction.

The tracking device 101 comprises a probe beam projector 30, a beam splitter 3, a pair of cross polarizers 2 and 6, a photo-detector assembly 7, and an analyzing electronics 50. The eye pupil 15 is used as a symmetric reference mark 20. The probe beam projector 30 projects a probe beam 4 scanning across the reference mark 20. The scanning probe beam 4, as shown in FIG. 1, scans along a horizontal direction that is perpendicular to a vertical symmetric line of the eye pupil 15. The scanning probe beam 4 starts repeatedly from a fixed point and scans at a constant speed over a predetermined scanning length. The probe beam projector 30 also produces a reference signal 31 to indicate a reference point of each scan.

The probe beam 30 is optically located near the eye axis. The beam splitter 3 is disposed to reflect the backward scattered light 5 into the photo-detector assembly 7. The cross polarizers 2 and 6 are used to reject reflection from the corneal surface. The photo-detector assembly 7 receives and converts the scattered light 5 into an electrical signal, i.e., scattered-light signal 8. Due to the cat eye or red eye effect, the backward scattering from the eye pupil 15 is much stronger than that from the iris 14. That is, the eyeball behaves more or less as a retro-reflector. Hence, the intensity of the backward scattered light 5 increases significantly as the probe beam 4 scans from the iris 14 to the pupil 15 and decreases significantly as the probe beam 4 scans from the pupil 15 to the iris 14. This intensity change of the scattered light 5 generates a square-like pulse in the scattered-light signal 8. The timing of the pulse center depends on the position of the eye 10, while the width of the square-like pulse depends on the size of the pupil 15.

In one implementation, an infrared laser beam (at 830 nm) of about 100 $\mu$W is used for the scanning probe beam 4 and the photo-detector assembly 7 having an aperture of about 18 mm is located about 30 cm away from the eye 10. The photo-detector assembly 7 receives a scattered light power of about 35 nW when the probe beam 4 is on the pupil 15 and of about 5 nW when the probe beam 4 is on the iris.

FIG. 1a shows timing diagrams of the scattered-light signal 8 and the reference signal 31. The scattered-light signal 8 has a sequence of square-like pulses 9 and each square-like pulse 9 corresponds to a scan of the probe beam 4 across the pupil 15. The timing center Tc of each square-like pulse 9 has a time delay Td with respect to a reference time Tr of the reference pulse 31s. This time delay Td depends on the position of the y-axis in the x direction and varies as the eye 10 moves.

The analyzing electronics 50, which may include a microprocessor, analyzes the square-like pulses to determine the timing center Tc of each square-like pulse 9. The analyzing electronics 50 then calculates the time delay Td of Tc with respect to the reference pulse 31s for each scan. Because the probe beam 4 scans at a constant speed, this time delay Td can be translated proportionally to a displacement of the symmetric line with respect to a reference position. This time delay Td is then used to determine the position of the symmetric line of the pupil 15 and thus the eye position along the scanning direction of the probe beam 4

To operate the tracking device 101 and the surgical beam delivery system 100, an initial time delay $Td_0$ or eye position is first registered and stored in the system computer 80. The time delay Td of subsequent scans is then compared with the initial time delay $Td_0$ to calculate a displacement of the eye 10. With this calculated displacement, the system computer 80 generates a control signal 81 to drive the beam steering module 60 to steer the surgical laser beam 62 to follow the movement of the eye 10.

As an open loop device, the scanning probe beam 4 does not move with the eye 10. The beam steering module 60 can be used simultaneously to compensate the eye movement and to scan the surgical laser beam 62 on the eye 10. In this case, the control signal 81 may consist of a scanning signal and an offset signal. The scanning signal scans the surgical laser beam 62 in a predetermined pattern while the offset signal offsets the surgical laser beam 62 to compensate for the eye movement.

Due to the symmetric nature of the pupil 15, the probe beam 4 scanning along the horizontal direction (i.e. the x-axis) determines the horizontal position of the y-axis of the pupil 15, regardless the vertical position of the pupil 15. Therefore, within the vertical size limit, the horizontal detection of pupil 15 is independent to the vertical movement of the eye 10. Similarly, the vertical detection of pupil 15 is independent to the horizontal position of the eye 10. In other words, the tracking range of the pupil-tracking device 101 in the open loop configuration is as big as the pupil size.

The same tracking device 101 can be easily implemented into a closed loop configuration. Generally, open loop configuration is more desirable for its simplicity and its feasibility to separate the optical path for position sensing from the optical path for the surgical laser beam. Closed loop configuration may be chosen for its reliability and for a tracking range larger than the pupil size.

Figure 2:
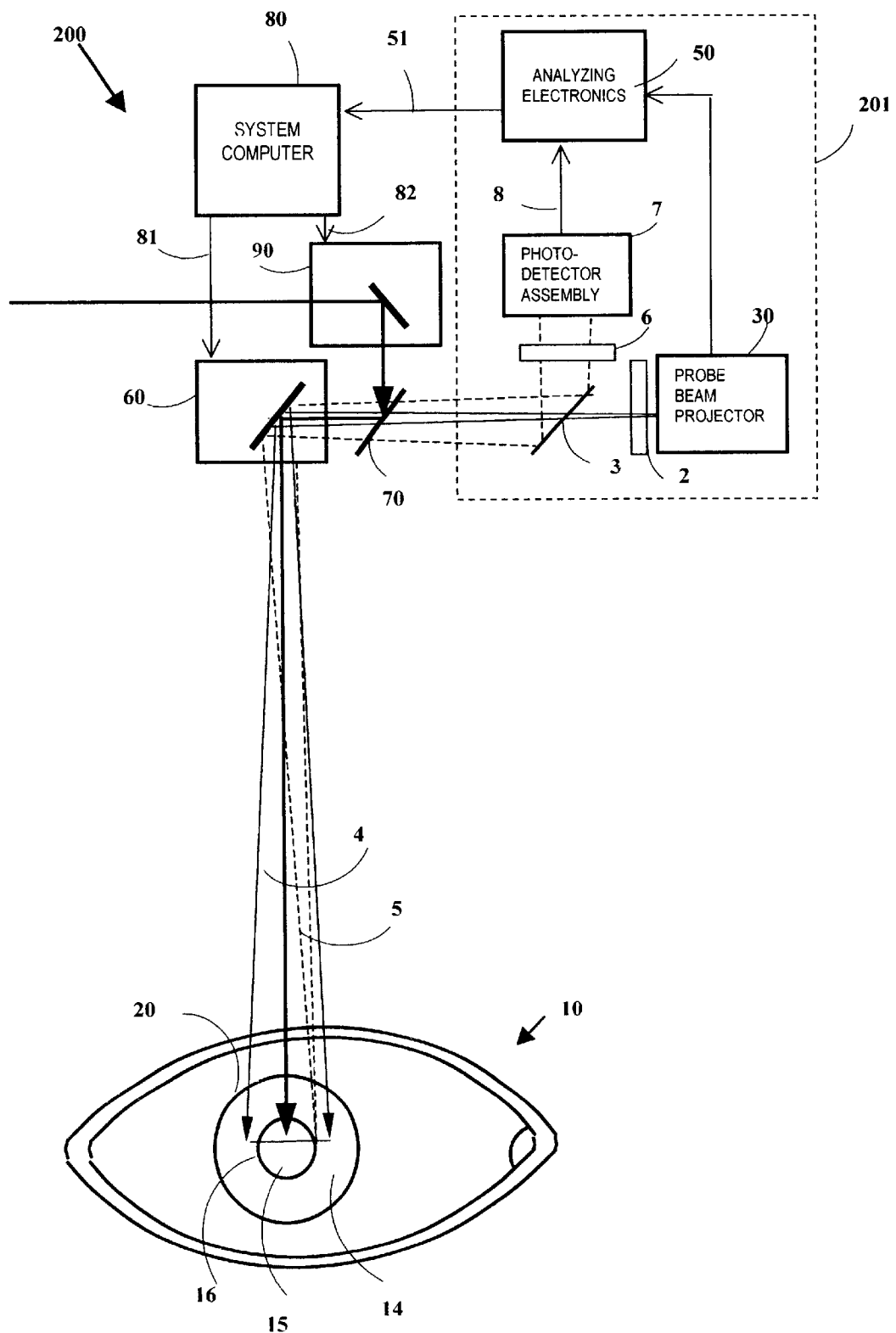
FIG. 2 shows a schematic diagram of an optical tracking device in a closed loop configuration for a surgical laser beam delivery system.

FIG. 2 shows a schematic diagram of the tracking device 201 used in a closed-loop configuration for a surgical beam delivery system 200. In the closed-loop configuration, both the scanning beam 4 and the surgical beam 62 are steered to the eye 10 by a common steering module 60. Consequently, both the scanning probe beam 4 and the surgical laser beam 62 follow the movement of the eye 10.

In implementation, the scanning probe beam 4 is directed into the beam steering module 60 and reflected onto the symmetric reference mark 20 (i.e. the eye pupil 15). A dichromatic mirror 70 is placed in the path of the scanning probe beam 4 to couple the surgical laser beam 62 into the beam steering module 60. The dichromatic mirror 70 reflects light at the wavelength of the surgical laser beam 62 but transmits light at the wavelength of the scanning probe beam 4. Both the surgical laser beam 62 and the scanning probe beam 4 are reflected from the beam steering module 60 and projected onto the eye 10.

Again, the backward scattered light 5 from the symmetric reference mark 20 is reflected by beam splitter 3 and detected by a photo-detector assembly 7, which produces an output of scattered-light signal 8. Similar to the open loop device 100, the scatted-light signal 8 comprises a sequence of square-like pulses 9, of which each corresponding to a scan of the probe beam 4 across the symmetric reference mark 20. The center of each square-like pulse 9 has a time delay Td with respect to the reference point 31 s of corresponding scan. An analyzing electronics 50 determines the timing center Tc of each square-like pulse and then the time delay Td for each scan.

To operate the tracking device 201 and the surgical beam delivery system 200, an initial time delay $Td_0$ or eye position is first registered and stored by the system computer 80. The time delay Td of later scans is then compared with the initial time delay $Td_0$. Any deviation of Td from $Td_0$ is used as an error signal to drive the beam steering module 60 such that to bring the error signal toward zero. Through this process, the beam steering module 60 deflects the scanning probe beam 4 to follow the movement of the eye 10. Seeing the same deflection as the scanning probe beam 4, the surgical laser beam 62 can thus impinge on any predetermined position of the eye 10 as if the eye remains stationary.

As a closed loop device, the relative position between the trace of the scanning probe beam 4 and the symmetric reference mark 20 is kept constant during the operation. The beam steering module 60 is thus used solely for compensating the eye movement. A second beam steering module 90 is required to scan the surgical laser beam 62 on the eye 10 for surgery purpose. In this case, the control signal 81 to beam steering module 60 is simply the driving signal to compensate the eye movement. The control signal 82 to beam steering module 90 is simply the programmable signal to scan the surgical laser beam 62. The closed loop device 200 is relatively more complicate but it can work fine even when the reference mark has less than perfect symmetry.

FIG. 3 shows a probe beam projector 30 that produces and scans a probe beam 4. The projector 30 includes a line beam generator 40 and a rotating cylinder 35. The line beam generator 40 produces a collimated line beam 33 projected onto the rotating cylinder 35. The cylinder 35 has a set of slits 36 evenly distributed on its wall. A motor 34 drives the cylinder 35 at a constant rotation speed. The slits 36 are thus scanned across the line beam 33 at a constant speed.

As the slits 36 scan across the line beam 33 consecutively, a narrow beam 38 passing through the slits 36 scans across the reference mark 16 repeatedly. Thus, this narrow beam 38 may serve as the scanning probe beam 4 of FIG. 1.

A beam splitter 39 directs a small portion of the beam 38 onto a reference photo-detector 32. This reference photo-detector 32 has a tiny light-sensitive area and the detected signal is thus a sequence of spikes as the split beam scans across the reference detector 32 repetitively. The output signal from the photo-detector 32 defines a reference point of the scanning and serves as the reference signal 31 of FIG. 1.

FIG. 3a shows schematically a line beam generator 40. In this embodiment, the line beam generator 40 consists of a diode laser 41, a holographic diffuser 43, and a cylindrical lens 45. The diode laser 41 produces a collimated laser beam 42 at a predetermined wavelength and power. The holographic diffuser 43 works as a line generator and diffracts the beam 42 evenly into a beam 44 that fans out in a plane. The cylindrical lens 45 collimates the beam 44 into a line beam 33. A line generator with a holographic diffuser is well known to those skilled in the art.

The scanning rate of the probe beam projector 30 can be up to the kilohertz range. For example, the motor 34 may run at 100 cycles per second and the cylinder 35 may have 10 slits 36 on it.

Figure 4:
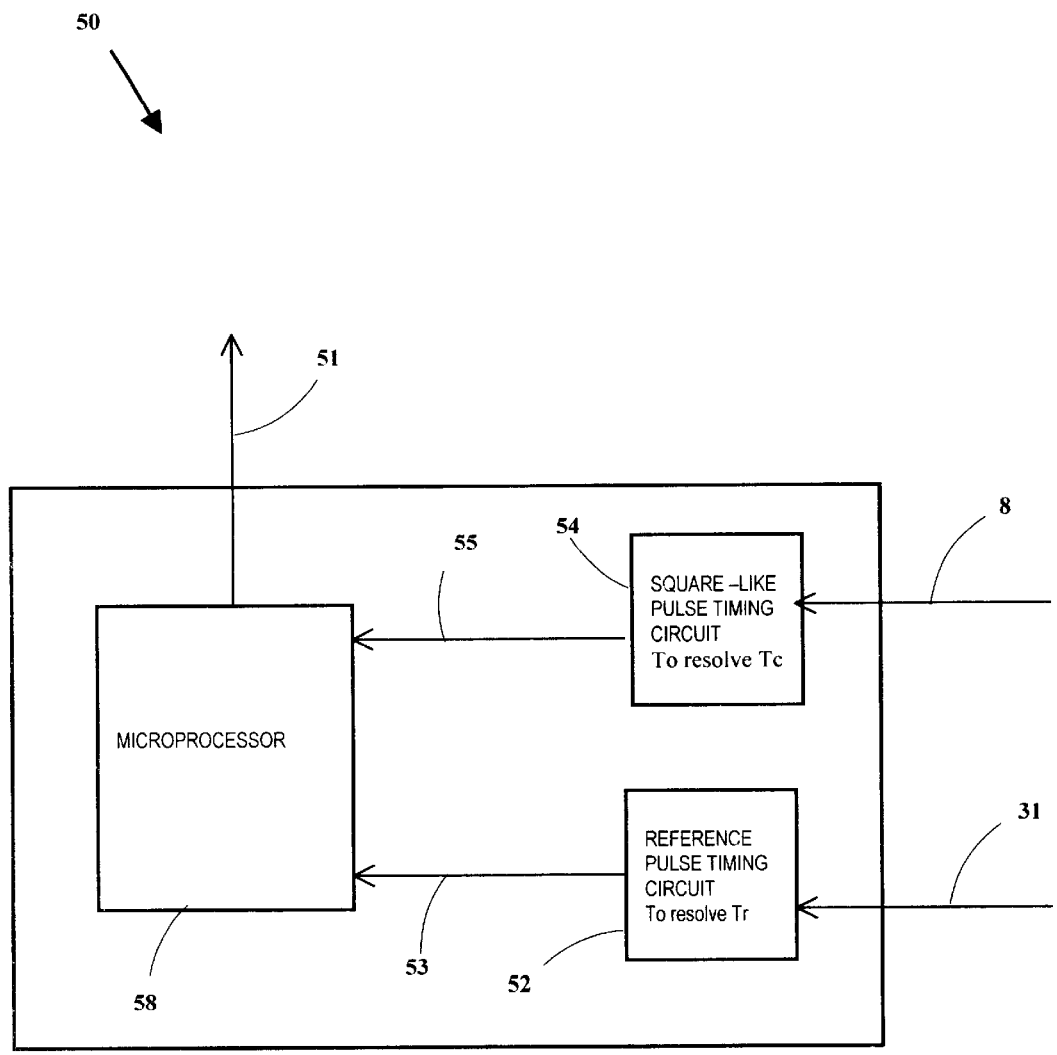
FIG. 4 is a block diagram showing an analyzing electronics for the optical tracking device.

FIG. 4 is a block diagram showing one embodiment of the analyzing electronics 50. This analyzing electronics 50 includes a reference pulse timing circuit 52, a square-like pulse timing circuit 54, and a microprocessor 58. The reference signal 31 from the probe beam projector 30 is fed into the reference pulse timing circuit 52 to produce a TTL output signal 53 carrying the timing Tr of the reference signal 31. The scattered-light signal 8 from the photo-detector assembly 7 is fed into the square-like pulse timing circuit 54 to produce a TTL output signal 55 carrying the timing center Tc of the square-like pulses of the scattered-light signal 8. Spike-pulse timing circuit 52 and square-like pulse timing circuit 54 are known to those skilled in the art.

The microprocessor 58 reads in the signal 53 and signal 55 to calculate a time delay Td between the two signals. This time delay Td indicates the relative position of the symmetric reference mark 20 to the scanning probe beam 4. This delay Td is then to compare with an initial delay $Td_0$ registered and stored by the system computer 80 at an initial time of the tracking.

For the tracking device 101 used in an open loop configuration of surgical beam delivery system 100, any change of the delay Td from its initial value $Td_0$ can be used to determine a displacement of the eye 10 from its initial position. The determined displacement can then be converted into an offset signal combined in the control signal 81 to deflect the surgical laser beam 62 to follow the movement of the eye 10

For the tracking device 201 used in a closed loop configuration of surgical beam delivery system 200, any deviation of the delay Td from its initial value $Td_0$ is used as an error signal to drive the beam steering module 60 such that to bring the error signal toward zero. The beam steering module 60 thus deflects both of the scanning probe beam 4 and the surgical laser beam 62 to follow the movement of the eye 10.

The above-described operation of the analyzing electronics 50 is repetitively for every scan of the probe beam 4. The reference pulse timing circuit 52 and the square-like pulse timing circuit 54 should be reset automatically after the signal 53 and signal 55 are read by the microprocessor 58.

The analyzing electronics 50 shown in FIG. 4 is for one axis tracking. To track the two-dimensional movement of the eye 10, another set of the analyzing electronics should be used.

Figure 5:
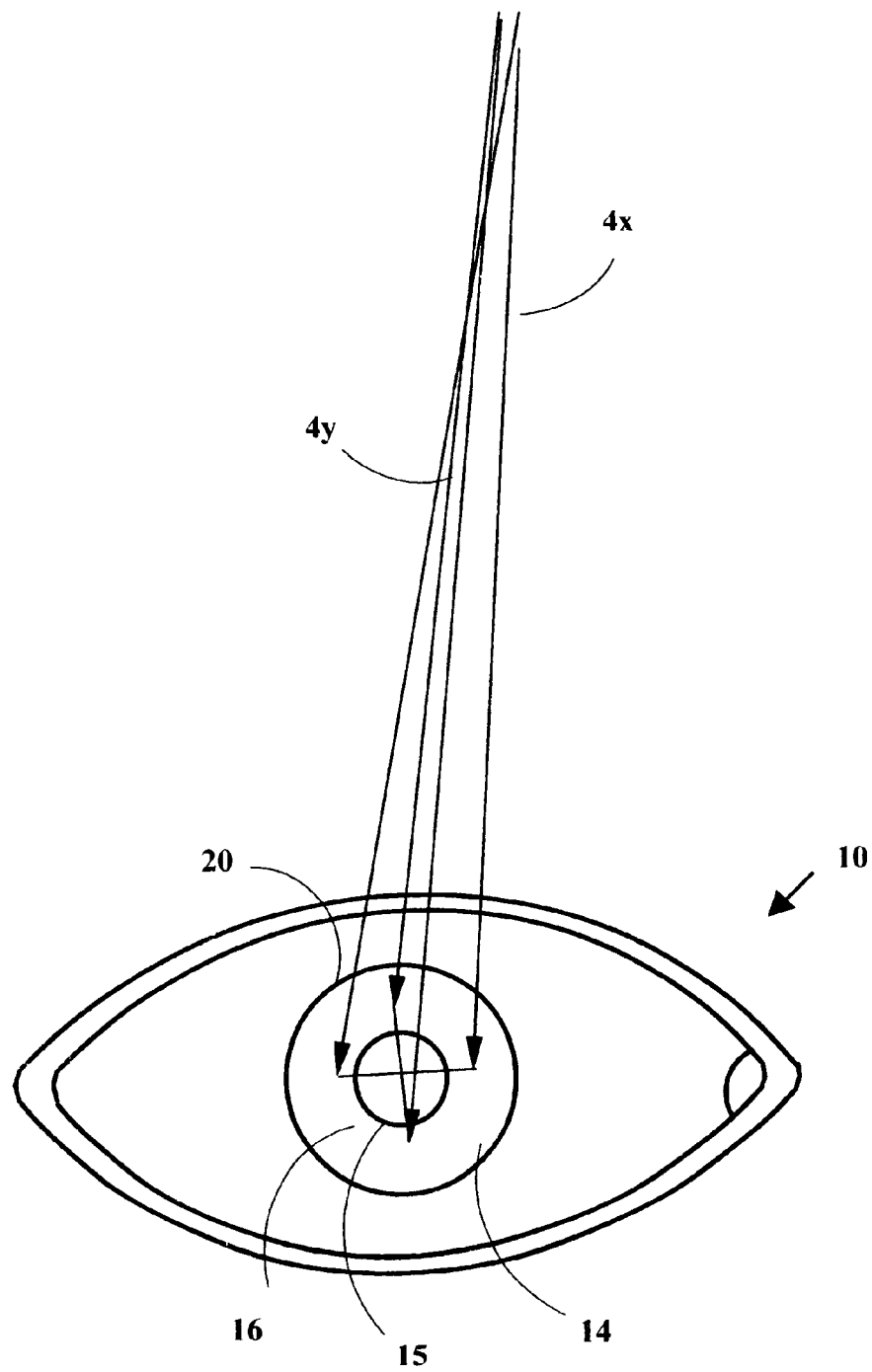
FIG. 5 is a schematic diagram illustrating simultaneous tracking of an eye in two different directions by two probe beams projected on and scanning across the pupil of a subject eye.

FIG. 5 shows schematically two scanning probe beams 4x and 4y projected on a symmetric reference mark 20 (the eye pupil 15) for two-dimension positioning detection. The two scanning probe beams 4x and 4y are set along two directions, of which each is perpendicular to a symmetric line of the pupil 15.

For eye safety and conformity, the probe beams 4x and 4y shall have each a power less than 100 $\mu$W and a wavelength in the range of 700–1500 nm. To minimize the effect of cornea reflection to the scattered light signal 8, beam splitter 3 can be a polarized beam splitter. To avoid cross talking in a closed loop configuration, the two probe beams 4x and 4y can be projected alternatively in time. The scattered light from the two probe beams 4x and 4y can be detected with a single photo-detector assembly 7 and the scattered light signal 8 can then be separated for the two probe beams 4x and 4y in a time domain.

In all the above description, the tracking device is for steering a surgical laser beam 62 to follow the eye movement. Obviously, the same tracking mechanism can guide any other light beam or simply an optical path to follow the eye movement. Therefore, the above technique can be used to other surgical or diagnosis applications in which compensating the eye movement is desirable.

Although the above embodiments are described with a specific reference to pupil tracking, the present invention can be further extended to a method to track lateral movement of other object having a symmetric reference mark. In a general method of tracking, the cat eye effect is not necessary available and the symmetric reference mark shall have at least two symmetric lines that may or may not be orthogonal to each other.

Figure 6:
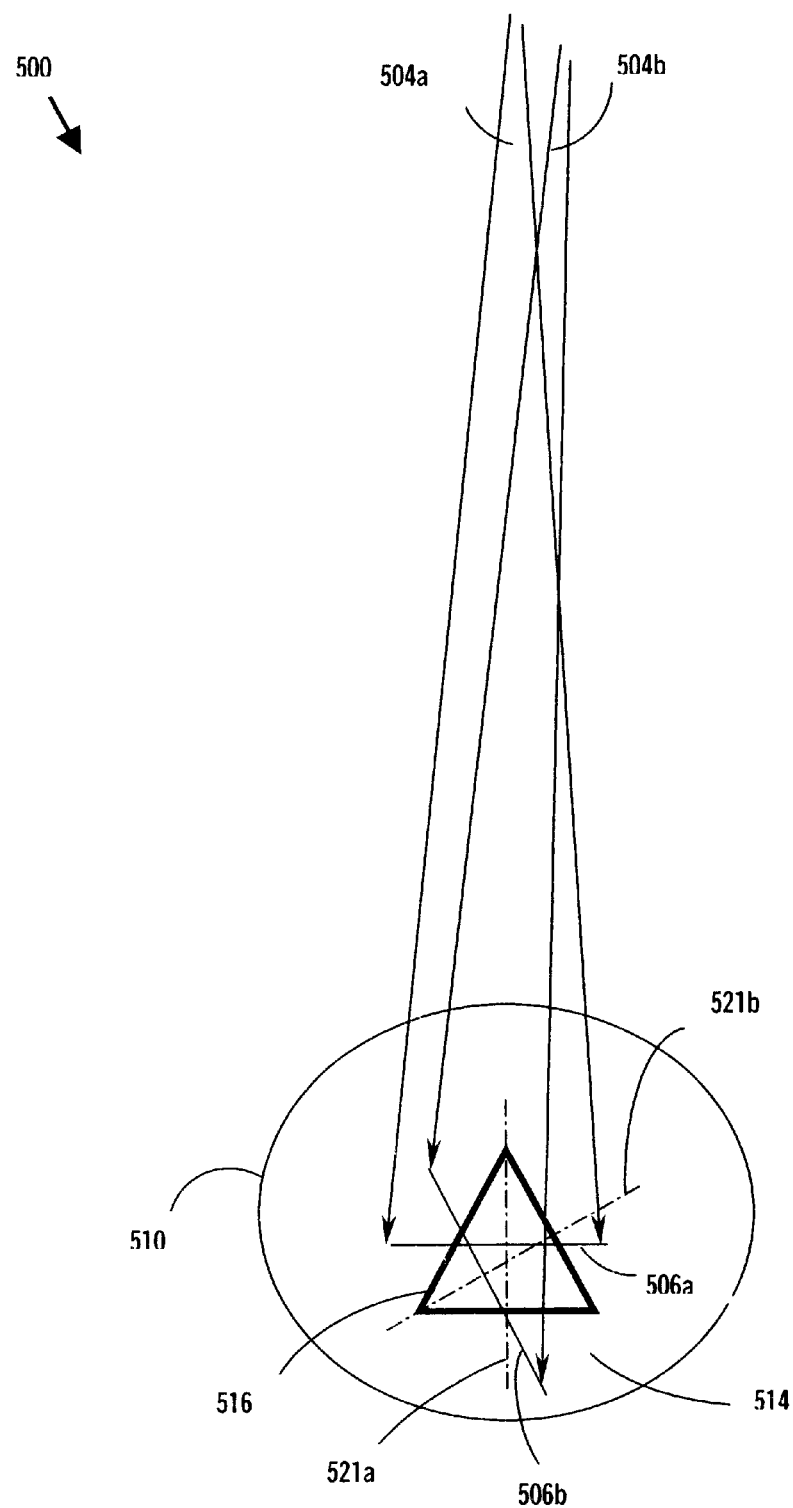
FIG. 6 is a schematic diagram showing optical tracking of a symmetric reference mark having at least two symmetric lines, in accordance with the present invention.

FIG. 6 is a schematic diagram 500 showing optical tracking of a symmetric reference mark 516 having at least two symmetric lines 521a and 521b. To implement, two probe-beams 504a and 504b are projected onto an object 510 to be tracked. These two probe beams 504a and 504b scan repeatedly along two directions 506a and 506b that are perpendicular respectively to the two symmetric lines 521a and 521b of the symmetric reference mark 516.

In a first situation, the reflectance inside the reference mark 516 is substantially higher than that of its surrounding area 514. Each probe beam 504a or 504b scans repeatedly across the symmetric reference mark 516 and thus the photo-detector detected the scattered light generates a train of square-like pulses. The timing center of each pulse indicates the instant position of the related symmetric line 521a or 521b. An analyzing electronics is used to determine the timing center of each of the consecutive pulses and thus to determine the position of the symmetric line 521a (or 521b) perpendicular to the scanning direction 506a (or 506b) of the probe beam 504a (or 504b). The position detection of the symmetric line 521a (or 521b) is independent from the object's movement along the direction of the symmetric line. This way the positions of the two symmetric lines 521a and 521b can be detected independently in an open loop configuration. As a result, the crossing point between the two symmetric lines 521a and 521b can be determined so as to track the lateral position of the object 510. As shown in FIG. 6, the symmetric lines 521a and 521b may or may not be perpendicular to each other. The tracking range of this detection is substantially as big as the size of the symmetric reference mark 516.

In a more general situation, the reflectance inside the reference mark 516, on the boundary of the reference mark 516, and in its surrounding area 514 can be significantly different from each other. Considering the symmetric nature of the reference mark, the scattered light signal for each scan shall have a substantially symmetric profile and the timing center of each symmetric-profile signal corresponds to the position of the symmetric line of the scan.

The scattered lights from the two probe beams 504a and 504b usually overlap each other spatially. To achieve independent detection of positions of the symmetric lines 521a and 521b, the two probe beams 504a and 504b can be projected alternatively in time. The scattered lights from the two probe beams 504a and 504b can be detected with a single photo-detector and the scattered light signal can then be separated for the two probe beams 504a and 504b in a time domain.

Although the present invention has been described with specific reference to embodiments, by way of illustration and for clarity of understanding, various modifications can be made without departing from the scopes of the appended claims.

What is claimed is:

1. An apparatus for tracking lateral movement of an object having a reference mark with at least two symmetric lines, comprising:

a first probe beam projector to project and to scan a first probe beam repeatedly on said reference mark of said object, wherein said first probe beam is scanned perpendicularly to a first symmetric line of said reference mark, wherein said first probe beam projector also produces a first reference pulse for each scan of said first probe beam;

a second probe beam projector to project and to scan a second probe beam repeatedly on said reference mark of said object, wherein said second probe beam is scanned alternatively with said first probe bean and perpendicularly to a second symmetric line of said reference mark, wherein said second probe beam projector also produces a second reference pulse for each scan of said second probe beam;

a photo-detection means receiving scattered light from said object to produce a scattered-light signal consisting of a sequence of symmetric-profile signals, of which each symmetric-profile signal corresponds to a scan of said first or said second probe beam and indicates with the timing center of said each symmetric-profile signal the instant position of a symmetric line perpendicular to said scan; and an analyzing electronics coupled to said first probe beam projector, said second probe beam projector, and said photo-detection means to generate a first output signal and a second output signal, wherein said first output signal indicates the position change of said first symmetric line with respect to a first reference position so as to track movement of said object along the scanning direction of said first probe beam, and wherein said second output signal indicates the position change of said second symmetric line with respect to a second reference position so as to track movement of said object along the scanning direction of said second probe beam.

2. An apparatus as in claim 1, further comprising:
a beam steering module coupled to said analyzing electronics and directing an optical path onto said object;
wherein said beam steering module is driven to direct said optical path to follow the movement of said object.

3. An apparatus as in claim 1, wherein said object is a subject eye and said reference mark is the pupil.

4. An apparatus as in claim 1, wherein said object is a subject eye and said reference mark is the limbus.

5. An apparatus as in claim 1, wherein each of said first probe beam projector and said second probe beam projector consists of a linear light beam and plurality of moving slits.

6. An apparatus as in claim 1 wherein each of said first probe beam and said second probe beam has a wavelength in the range of 700–1500 nm.

7. An apparatus as in claim 1 wherein said photo-detection means includes a focal lens and a photo detector.

8. An apparatus as in claim 1 wherein said scattered light from said first probe beam and said second probe beam is separated in the time domain.

9. An apparatus as in claim 1 wherein said first symmetric line and said second symmetric line are or are not orthogonal to each other.

10. An apparatus as in claim 2 wherein said first probe beam and said second probe beam are arranged in an open-loop configuration.

11. An apparatus as in claim 2 wherein said first probe beam and said second probe beam are arranged in a closed-loop configuration.

12. A method for optically tracking lateral movement of an object, comprising the steps of:
selecting a reference mark on said object, said reference mark has at least two symmetric lines;
scanning repeatedly a first probe beam perpendicular to a first symmetric line of said reference mark;
producing a first reference signal synchronized with said first probe beam to represent a first reference position for each scan;
scanning repeatedly a second probe beam perpendicular to a second symmetric line of said reference mark, wherein said second probe beam is scanned alternatively with said first probe beam;
producing a second reference signal synchronized with said second probe beam to represent a second reference position for each scan of said second probe beam;
detecting scattered light from said object to produce a scattered-light signal consisting of a sequence of symmetric-profile signals;
separating said sequence of symmetric-profile signals between said first probe beam and said second probe beam, through synchronization with said first and said second reference signals;
determining the timing center of each symmetric-profile signal to determine the instant positions of said first and second symmetric lines;
recording a first initial position of said first symmetric line and a second initial position of said second symmetric line;
comparing said instant position of said first symmetric line with said first initial position to produce a first output signal indicating the relative position change of said first symmetric line; and
comparing said instant position of said second symmetric line with said second initial position to produce a second output signal indicating the relative position change of said second symmetric line.

13. A method as in claim 12, further comprising the steps of:
providing a beam steering module directing an optical path to said object; and
controlling said beam steering module according to said first output signal and said second output signal so that the direction of said optical path is compensated for the movement of said object.

14. An apparatus for tracking lateral movement of an eye pupil, comprising:
a first probe beam projector to project and to scan a first probe beam repeatedly on said eye pupil, wherein said first probe beam is scanned perpendicularly to a first symmetric line of said eye pupil, and wherein said first probe beam projector also produces a first reference pulse for each scan of said first probe beam;
a second probe beam projector to project and to scan a second probe beam repeatedly on said eye pupil, wherein said second probe beam is scanned alternatively with said first probe bean and perpendicularly to a second symmetric line of said eye pupil, and wherein said second probe beam projector also produces a second reference pulse for each scan of said second probe beam;
a photo-detection means receiving scattered light from said eye pupil to produce a scattered-light signal consisting of a sequence of square-like pulses, of which each square-like pulse corresponds to a scan of said first or said second probe beam and indicates with the center of said square-like pulse the instant position of said first or second symmetric line correlated to said scan; and
an analyzing electronics coupled to said first probe beam projector, said second probe beam projector, and said photo-detection means to generate a first output signal and a second output signal, wherein said first output signal indicates the position change of said first symmetric line of said eye pupil with respect to a first reference position so as to track movement of said eye pupil along the scanning direction of said first probe beam, and wherein said second output signal indicates the position change of said second symmetric line of said eye pupil with respect to a second reference position so as to track movement of said object along the scanning direction of said second probe beam.

15. An apparatus as in claim 14, further comprising:
a beam steering module coupled to said analyzing electronics and directing an optical path onto said object;
wherein said beam steering module is driven to direct said optical path to follow the movement of said eye pupil.

16. An apparatus as in claim 14 wherein said first symmetric line and said second symmetric line are chosen to be perpendicular to each other.

17. An apparatus as in claim 14 wherein said first symmetric line and said second symmetric line are chosen to be horizontal and vertical lines.

18. An apparatus as in claim 14 wherein said optical path represents a surgical laser beam.

19. An apparatus as in claim 14 wherein said optical path represents a diagnosis light beam or an observation path.

* * * * *